US009766122B2

(12) United States Patent
Cothuru et al.

(10) Patent No.: US 9,766,122 B2
(45) Date of Patent: Sep. 19, 2017

(54) METHOD AND SYSTEM FOR POSITIONING AN APPARATUS FOR MONITORING A PARABOLIC REFLECTOR AERIALLY

(75) Inventors: Santhosh Kumar Cothuru, Bangalore (IN); Siraj Issani, Bangalore (IN); Vishal Prabhu, Bangalore (IN); Ganapathi Subbu Sethuvenkatraman, Maduaral (IN)

(73) Assignee: SIEMENS AKTIENGESELLSCHAFT (DE)

( * ) Notice: Subject to any disclaimer, the term of this patent is extended or adjusted under 35 U.S.C. 154(b) by 639 days.

(21) Appl. No.: 14/347,311

(22) PCT Filed: Sep. 13, 2012

(86) PCT No.: PCT/EP2012/067972
§ 371 (c)(1),
(2), (4) Date: Jun. 24, 2014

(87) PCT Pub. No.: WO2013/050227
PCT Pub. Date: Apr. 11, 2013

(65) Prior Publication Data
US 2014/0332688 A1    Nov. 13, 2014

(30) Foreign Application Priority Data

Oct. 5, 2011  (IN) ............................ 1297/KOL/2011
Feb. 9, 2012  (EP) ..................................... 12154762

(51) Int. Cl.
*F24J 1/00*  (2006.01)
*G01J 1/04*  (2006.01)
(Continued)

(52) U.S. Cl.
CPC ............ *G01J 1/0403* (2013.01); *B64C 19/00* (2013.01); *F24J 2/14* (2013.01); *F24J 2/4607* (2013.01);
(Continued)

(58) Field of Classification Search
CPC ................................... F24J 2/14; G01J 1/0403
(Continued)

(56) References Cited

U.S. PATENT DOCUMENTS 3,518,004 A    6/1970   Brewer
4,469,938 A    9/1984   Cohen
(Continued)

FOREIGN PATENT DOCUMENTS

CN    101261520 A    9/2008
CN    101667032 A    3/2010
(Continued)

OTHER PUBLICATIONS

PCT/EP2012/067972 International Search Report and Written Opinion. Date of Mailing: Jan. 25, 2013. Siemens Aktiengesellschaft (12 pages).
(Continued)

*Primary Examiner* — Avinash Savani
(74) *Attorney, Agent, or Firm* — Schmeiser, Olsen & Watts LLP

(57) ABSTRACT

A method and a system for positioning an apparatus for monitoring a parameter of one or more parabolic reflectors of a solar thermal field, wherein the method comprises positioning the apparatus at a first field location responsive to the position of the respective parabolic reflector, acquiring information of an absorber tube of the respective parabolic reflector, and positioning the apparatus at the second field location responsive to the information of the absorber tube, the second field location being beyond the focus of the respective parabolic reflector is provided.

15 Claims, 11 Drawing Sheets

(51) Int. Cl.
*F24J 2/14* (2006.01)
*F24J 2/46* (2006.01)
*G01M 11/00* (2006.01)
*G01B 11/24* (2006.01)
*B64C 19/00* (2006.01)
*G01N 21/01* (2006.01)
*H02S 50/00* (2014.01)
*F24J 2/38* (2014.01)

(52) U.S. Cl.
CPC ........... *G01B 11/24* (2013.01); *G01M 11/005* (2013.01); *G01N 21/01* (2013.01); *H02S 50/00* (2013.01); *F24J 2002/385* (2013.01); *F24J 2200/00* (2013.01); *Y02E 10/45* (2013.01)

(58) Field of Classification Search
USPC ........................................................ 126/694
See application file for complete search history.

(56) References Cited

U.S. PATENT DOCUMENTS

| | | | |
|---|---|---|---|
| 5,982,481 A | 11/1999 | Stone et al. | |
| 7,667,833 B1 | 2/2010 | Diver | |
| 2006/0149458 A1 | 7/2006 | Costello et al. | |
| 2009/0107485 A1* | 4/2009 | Reznik | F24J 2/07 126/600 |
| 2010/0000517 A1 | 1/2010 | Zalusky | |
| 2010/0002237 A1 | 1/2010 | Zalusky | |
| 2013/0021471 A1* | 1/2013 | Waterhouse | F24J 2/38 348/139 |

FOREIGN PATENT DOCUMENTS

| | | |
|---|---|---|
| DE | 10056070 A1 | 6/2002 |
| DE | 10238202 A1 | 3/2004 |
| DE | 10238202 B4 | 4/2005 |
| EP | 1717568 A2 | 11/2006 |
| EP | 1717568 B1 | 7/2012 |

OTHER PUBLICATIONS

European Search Report for European Application No. 12154762.4 Date of Mailing: Jan. 23, 2013. Siemens Aktiengesellschaft (7 pages).

* cited by examiner

METHOD AND SYSTEM FOR POSITIONING AN APPARATUS FOR MONITORING A PARABOLIC REFLECTOR AERIALLY

CROSS-REFERENCE TO RELATED APPLICATIONS

This application claims priority to PCT/EP2012/067972, having a filing date of Sep. 13, 2012 which claims priority to European Patent Application 12154762 having a filing date of Feb. 9, 2012 and Indian Patent Application 1297/KOL/2011, having a filing date of Oct. 5, 2011, the entire contents of each which are hereby incorporated by reference.

FIELD OF TECHNOLOGY

The following relates to Concentrated Solar Power (CSP) plants that have reflectors having a reflectivity of about 94% that concentrate incident solar radiation onto an absorber tube. The reflectors are generally parabolic reflectors. One example of a parabolic reflector is a parabolic trough. Efficiency of these types of plants depends on many parameters, for example, accumulation of dust on the surface of the reflector, misalignment of the surface of the reflector with the absorber tube. Accumulation of dust on the surface of the parabolic reflector reduces the reflection efficiency of the parabolic reflector which in turn reduces the efficiency of the plant. Misalignment of the surface of the parabolic reflector to the absorber tube also reduces the efficiency of the plant. Thus, solar power plants are required to be maintained in order to obtain increased efficiency.

BACKGROUND

One of the key maintenance activities in a solar power plant deploying parabolic reflectors is frequent washing of surface of the parabolic reflectors to remove the dust collected on the surface of the parabolic reflector. Three types of water washing techniques have been are reported in literature for washing the surface of the parabolic reflectors. The techniques include high volume pressure water spray, low volume high pressure spray and mechanical scrubbing along with water wash.

These processes are mostly automated, for example, some power plants use a movable arm to spray pressurized jet of water onto the surface of the parabolic reflector. In certain aspects, robotic systems can also be deployed. It is stated that automation is economical if the frequency of cleaning is less than a fortnight. Cleaning frequency varies based on period of the year (e.g. more in summer months). However, there is no guarantee whether the cleaning interval is optimum. Due to cost involved in cleaning the entire field at regular intervals and associated water consumption (some plants even use demineralized water), it is useful to identify a method to know if the parabolic reflectors require cleaning.

Automated methods to identify cleaning intervals for a power plant do not exist currently. There are some instruments based on optical techniques (scattering) that are available as a handheld device for flat mirrors, (e.g. heliostats) only. These instruments cannot however be used for parabolic mirrors due to their focusing geometry.

Conventional systems for monitoring parabolic reflectors require the use of ground systems with alignment fixtures. Thus for a solar thermal field alignment fixtures are required to be positioned at every parabolic reflector. Additionally, ground based systems required increased manual intervention.

SUMMARY

An aspect relates to an apparatus for monitoring one or more parameters of one or more parabolic reflectors of a solar thermal plant aerially.

An aspect relates to a method of positioning an apparatus for monitoring a parameter of one or more parabolic reflectors of a solar thermal field and a system for positioning an apparatus for monitoring a parameter of one or more parabolic reflectors of a solar thermal field, wherein the method comprises positioning the apparatus at a first field location responsive to the position of the respective parabolic reflector, acquiring information of an absorber tube of the respective parabolic reflector, and positioning the apparatus at the second field location responsive to the information of the absorber tube, the second field location being beyond the focus of the respective parabolic reflector.

The absorber tube is used as a marker for positioning the apparatus as the absorber tube 38 has a fixed location. This eliminates the requirement of positioning additional markers for determining the second field location. The information of the absorber can be acquired from the first field location as the first field location is at the vicinity of the parabolic reflector.

According to an embodiment, the method further comprises moving the apparatus at the second field location along a length of the respective parabolic reflector. This achieves in monitoring the parabolic reflector at multiple locations along its length.

According to another embodiment, the second field location is the center of curvature of the respective parabolic reflector. Positioning the apparatus at the center of curvature provides the advantage of detecting the maximum portion of the reflected light beam.

According to yet another embodiment, the step of positioning the apparatus at the second field location includes positioning the apparatus responsive to a position of the absorber tube. The position of the absorber tube is used as a reference for positioning the apparatus at the second field location.

According to yet another embodiment, the positioning of the apparatus responsive to the position of the absorber tube includes imaging the absorber tube with a wide field of view, aligning the absorber tube within a narrow field of view, and aligning the absorber tube at a reference coordinate within the narrow field of view for positioning the apparatus. From the first field location, the absorber tube is within the wide field of view of the imaging device. Thereafter, the absorber tube is aligned within the narrow field of view of the imaging device. Subsequently, the absorber tube is aligned at the reference coordinate within the narrow field of view. This achieves in positioning the apparatus at the second field of location responsive to the position of the absorber tube.

According to yet another embodiment, the reference coordinate corresponds to a center of the narrow field of view. Aligning the absorber tube to center of the narrow field of view achieves in positioning the apparatus at the center of curvature as the absorber tube is at the focus of the parabolic reflector.

According to yet another embodiment, the first field location and the second field location are beyond the focus of the respective parabolic reflector. This provides the advantage of monitoring the parabolic reflector with ease as the absorber tube does not pose any obstacle during monitoring.

According to yet another embodiment, the apparatus is positioned at the second field location aerially. Aerially monitoring the parabolic reflector reduces the human intervention required for monitoring the parabolic reflector.

Another embodiment includes, a system for positioning an apparatus for monitoring a parameter of one or more parabolic reflectors of a solar thermal field, wherein the system comprises a position estimation module configured to detect a position of the apparatus, a processing module operably coupled to the position estimation module to receive the position of the apparatus detected, a locomotion module operably coupled to the processing module, the processing module configured to control the locomotion module such as to position the apparatus at a first field location responsive to a position of the respective parabolic reflector, a local position estimation module configured to obtain an information of an absorber tube of the respective parabolic reflector, the processing module being further configured to receive the information of the absorber tube and configured to control the locomotion module to position the apparatus at the second field location.

According to an embodiment, the processing module is configured to control the locomotion module such that the apparatus is provided a motion at the second field location along a length of the respective parabolic reflector.

According to another embodiment, the second field location is the center of curvature of the respective parabolic reflector.

According to yet another embodiment, the processing module is configured to control the location module such that the apparatus is positioned at the second field location responsive to a position of the absorber tube.

According to yet another embodiment, the local position estimation module comprises an imaging device adapted to acquire an image of the absorber tube. This achieves in obtaining the information of the absorber tube.

According to yet another embodiment, the imaging device comprises a configurable field of view comprising a wide field of view and a narrow field of view and the processing module is configured to control the locomotion module to align the absorber tube within the wide field of view, to align the absorber tube within the narrow field of view and to align the absorber tube to a reference coordinate within the narrow field of view. The configurable field of view provides in positioning the apparatus at the second field location accurately.

According to yet another embodiment, the system is an unmanned aerial vehicle. The deployment of an unmanned aerial vehicle for positioning the apparatus for monitoring the parabolic reflector provides the advantage of reduced human intervention required for monitoring the parabolic reflector.

BRIEF DESCRIPTION

Some of the embodiments will be described in detail, with references to the following figures, wherein like designations denote like members, wherein.

Figure 1:
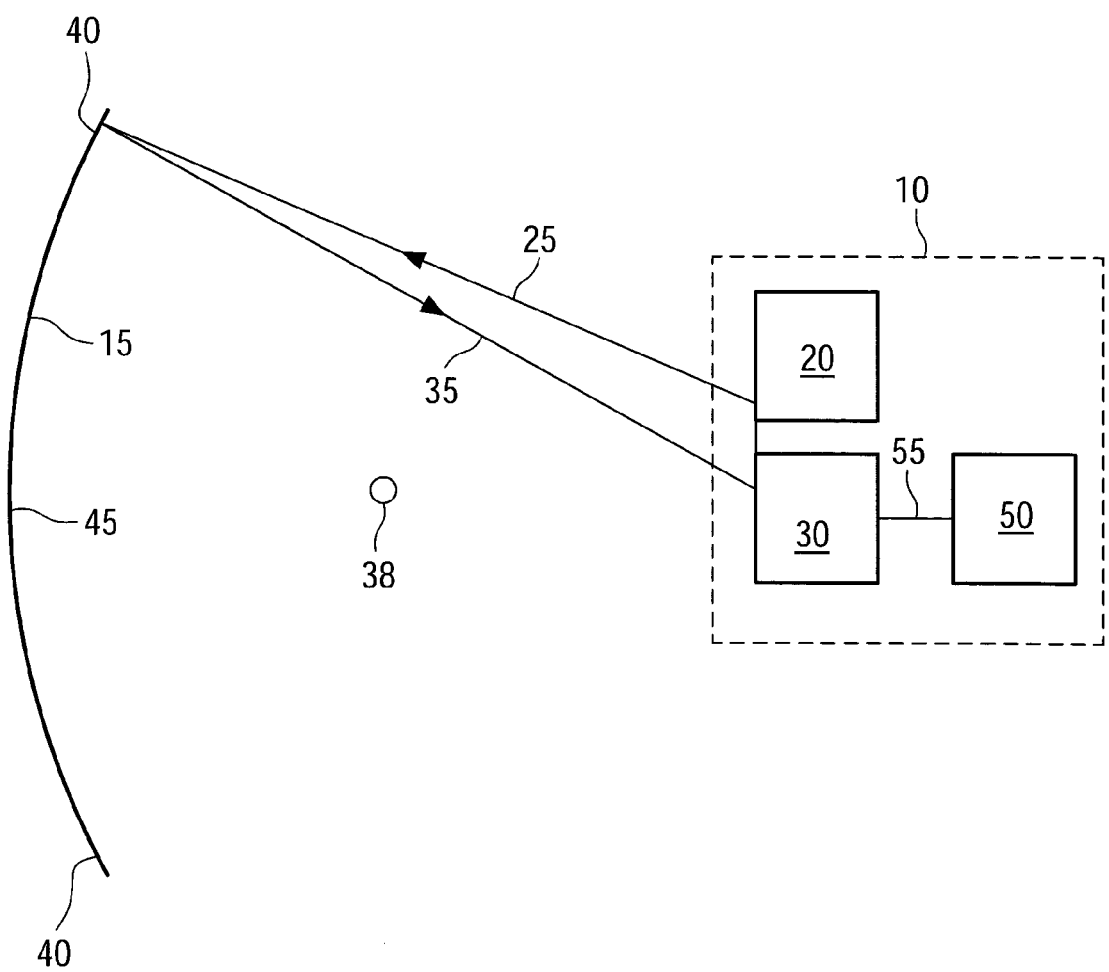
FIG. 1 depicts a schematic block diagram of an apparatus for monitoring a parameter of a parabolic reflector according to an embodiment herein.

Various embodiments are described with reference to the drawings, wherein like reference numerals are used to refer to like elements throughout. In the following description, for purpose of explanation, numerous specific details are set forth in order to provide a thorough understanding of one or more embodiments. It may be evident that such embodiments may be practiced without these specific details.

The embodiment of the invention is based on aerial monitoring of parabolic reflectors of a solar thermal plant. The apparatus for monitoring the parabolic reflectors are positioned aerially at the desired location for monitoring. The apparatus use changes in reflectivity of a surface of the parabolic reflector for monitoring the accumulation of dust on the surface. The alignment of the parabolic reflector to a focal point of the parabolic reflector is monitored by detecting the reflected light beam reflected by the parabolic reflector.

DETAILED DESCRIPTION

FIG. 1 illustrates an example of a schematic block diagram of an apparatus 10 for monitoring a parameter of a parabolic reflector 15 according to an embodiment herein. The parabolic reflector 15 in the shown example of FIG. 1 is a parabolic trough. The apparatus 10 comprises a light source 20 for directing a light beam 25 to be incident onto at least a portion of a surface of the parabolic reflector 15 and a detector 30 to detect the reflected light beam 35. As the surface of the parabolic reflector 15 is curved, the direction of the surface normal varies for each point on the surface of the parabolic reflector 15. Thus, the light source 20 is positioned such that the light beam 25 incident onto the parabolic reflector 15 is reflected back to the location where the detector 30 is positioned. For example this can be achieved by directing the light beam 25 from the light source 20 at an angle such that the reflected light beam 35 is captured by the detector 30. Thus, the light source 20 will be arranged into the apparatus 10 such that the light beam 25 is reflected to the location where the detector 30 is positioned.

Advantageously, as the apparatus 10 comprises the light source 20 and the detector 30, the apparatus 10 can be positioned at the location beyond the focus such that the reflected light beam 35 is detected at the detector 30. Beyond the focus herein is defined as the distance between the surface of the parabolic reflector and the detector 30 being greater than the focal length of the parabolic reflector 15.

Referring still to FIG. 1, the parameters that can be monitored by the apparatus 10, include, but, not limited to, a reflection efficiency of the parabolic reflector 15 and alignment of the parabolic reflector 15 to the focal point of the parabolic reflector 15. Advantageously, for monitoring the alignment of the parabolic reflector 15, the light beam 25 can be directed such that the light beam 25 is incident on at least a portion of the surface of the parabolic reflector 15 that is proximate to an edge 40 of the parabolic reflector 15 and distal from the center 45 of the parabolic reflector 15. This enables in determining the alignment of the surface of the parabolic reflector 15 with higher accuracy due to the curved geometry of the parabolic reflector 15. Advantageously, according to an aspect, for detecting the reflection efficiency, the light beam 25 can be incident nearby the center 45 of the parabolic reflector 15. This enables in detecting the accumulation of dust on the surface of the parabolic reflector 15 more accurately as in case the light beam 25 is incident proximal to the edge 40 of the parabolic reflector 15, the reflected light beam 35 may not be detected by the detector 30 in case the respective segment of the parabolic reflector is misaligned with the focal point.

Referring still to FIG. 1, an absorber tube 38 is arranged at a focus of the parabolic reflector 15 to receive the solar irradiation reflected by the parabolic reflector 15. The combination of the parabolic reflector 15 and the absorber tube 38 will hereinafter be referred to as a solar collector. The solar irradiation received by the absorber tube 38 is concentrated as the absorber tube 38 is positioned at the focus of the parabolic reflector 15. Thus, advantageously, the detector 30 and the light source 20 are positioned beyond the focus of the parabolic reflector 15 such that the reflected light beam 35 reflected by the parabolic reflector 15 can be detected at the detector 30. Thus, the apparatus 10 can be positioned beyond the focus of the parabolic reflector 15. This enables in easy monitoring of the parabolic reflector 15 as the apparatus 10 is not obstructed by the absorber tube 38. However, the light source 20 and the detector 30 can also be positioned within the focus also. However, in this case the absorber tube 38 may obstruct the monitoring of the parabolic reflector 15. Additionally, this enables in reducing the size of the apparatus as the light source 20 and the detector 30 can be positioned closely. Advantageously, the location beyond the focus can be the center of curvature of the parabolic reflector 15 as this provides the advantage of detecting the maximum portion of the reflected light beam 35. Moreover, the apparatus 10 does not obstruct the collection of solar irradiation reflected by the parabolic reflector 15 as the apparatus 10 is positioned beyond the absorber tube 38 for monitoring the parabolic reflector 15.

Referring still to FIG. 1, according to an aspect, the light source 20 can be a coherent light source such a as laser. The light beam 25 of the laser is directed at a spot on the parabolic reflector 15 and is reflected 35 back to the detector 30 positioned at the center of curvature of the parabolic reflector 15. A processing unit 50 is operably coupled to the detector 30 for receiving a single 55 responsive to the detected light beam and determine an intensity of the detected light beam by processing the signal 55. The processing unit 50 is configured to estimate a parameter of the parabolic reflector 15 by comparing the intensity of the detected light beam with a reference intensity.

Still referring to FIG. 1, for example, for parameters such as, but not limiting to, a reflection efficiency or an alignment of the parabolic reflector 15 to a focal point of the parabolic reflector 15, the intensity of the detected light beam will be of a reduced value than the reference intensity if there is an decrease in the reflection efficiency of the parabolic reflector 15 or the parabolic reflector 15 is misaligned with the focal point. In case of decrease in the reflection efficiency, the decrease is generally caused due to accumulation of dust on the surface of the parabolic reflector 15. Thus, the change in the reflection efficiency can be correlated to accumulation of dust on the surface of the parabolic reflector. Thus, the apparatus 10 can be implemented for monitoring the reflection efficiency or alignment of the parabolic reflector 15. The reference intensity can be stored at a memory internal to the processing unit 50 or external to the processing unit 50.

Referring still to FIG. 1, according to an aspect, the apparatus 10 can comprise two sets of the light source 20 and the detector 30, wherein one set is implemented for monitoring the reflection efficiency of the parabolic reflector 15 and the other set is implemented for monitoring the alignment of the parabolic reflector 15 to the focal point. This enables in monitoring the reflection efficiency of the parabolic reflector 15 and the alignment of the parabolic reflector 15 to the focal point simultaneously.

Figure 2:
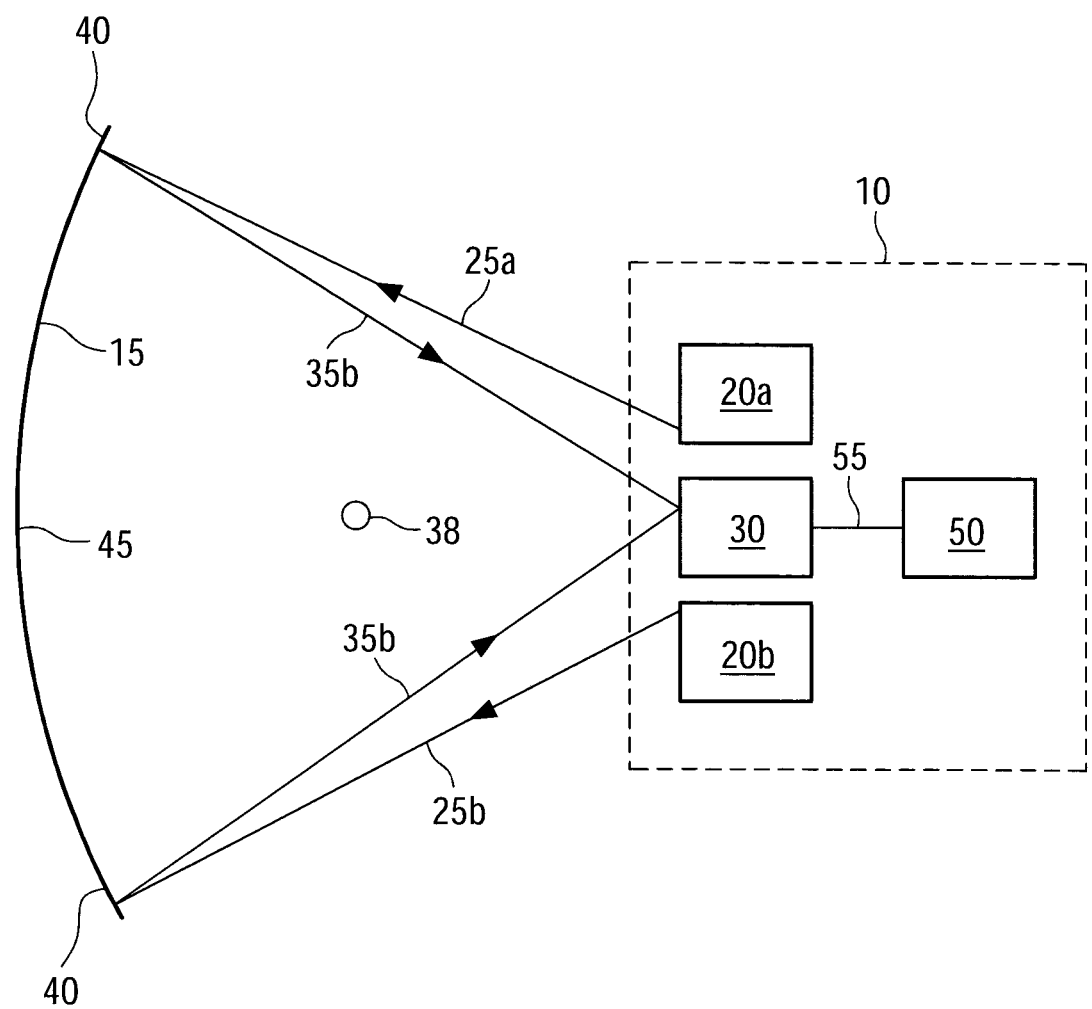
FIG. 2 depicts a schematic block diagram of an apparatus for monitoring a parameter of a parabolic reflector according to another embodiment herein.

FIG. 2 illustrates an example of a schematic block diagram of an apparatus 10 for monitoring a parameter of a parabolic reflector 15 according to another embodiment herein. In the shown example of FIG. 2, the apparatus 10 comprises a first light source 20a and a second light source 20b for directing respective light beams 25a, 25b on to the surface of the parabolic reflector 15. According to an aspect, as illustrated in the example of FIG. 2, the first light source 20a is configured such that the light beam 25a is incident onto a first portion on the surface of the parabolic reflector 15 and the second light source 20b is configured such that the light beam 25b is incident onto a second portion on the surface of the parabolic reflector 15. The first portion is proximal to the edge 40a and the second portion is proximal to the edge 40b of the parabolic reflector 15. The detector 30 is adapted to detect the reflected light beams 35a, 35b. Directing the lights beams 25a, 25b such that the light beams are incident onto two different portions proximal to the edges 40 of the parabolic reflector enables in monitoring the alignment of the parabolic reflector 15 with the focus with increased accuracy as the parabolic reflector 15 may comprise different segments. The light beams 25a, 25b being directed near the edges 40a, 40b increases the sensitivity of the misalignment detection and thus the accuracy.

Referring still to FIG. 2, in the present embodiment, the detector 30 is adapted to detect the reflected light beams 35a, 35b and output a signal 55 responsive to the detected light beams. The processing unit 50 is configured to receive the signal 55 and determine the intensity of the detected light beams by processing the signal 55. From the intensity of the detected light beams, the processing unit 50 is configured to estimate the one or more parameters by comparing the intensity detected with the reference intensity. According to an embodiment, the light sources 20a, 20b can be can be operated with a delay such that it can be easily known as to for which light source 20a, 20b the reflected light beam 35a, 35b is detected. This enables in further determining the segment of the parabolic reflector 15 for which the parameter is not optimum. According to an aspect, for parabolic reflectors 15 having a plurality of segments, a plurality of light sources 20 can be deployed to monitor the alignment of the respective segments. According to another aspect, a light source 20 can be configured to direct the light beam 25 such that the light beam 25 scans the different segments of the parabolic reflector 15.

Figure 3:
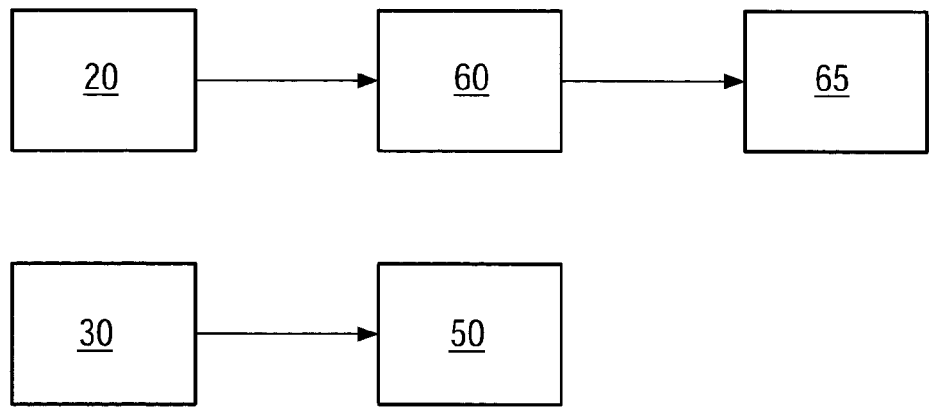
FIG. 3 depicts a block diagram of an apparatus for monitoring a reflection efficiency of a parabolic reflector according to another embodiment herein.

FIG. 3 illustrates an example of a block diagram of an apparatus 10 for monitoring a reflection efficiency of a parabolic reflector according to another embodiment herein. In the shown example of FIG. 3, the apparatus 10 comprises a light source 20, a diffuser 60, a beam splitter 65, a detector 30 and a processing unit 50. The diffuser 60 is adapted to diffuse the light beam emitted by the light source 20 and the beam splitter 65 is adapted to reflect the diffused light beam onto the parabolic reflector 15 of FIG. 2. Advantageously, the diffuser 60 and the light source 20 can be combined as a single unit. The reflected light beam is received by the beam splitter 65 and the beam splitter 65 is adapted to transmit the reflected light beam onto the detector 30. The apparatus 10 illustrated in FIG. 3 will be explained in detail in FIG. 4.

Figure 4:
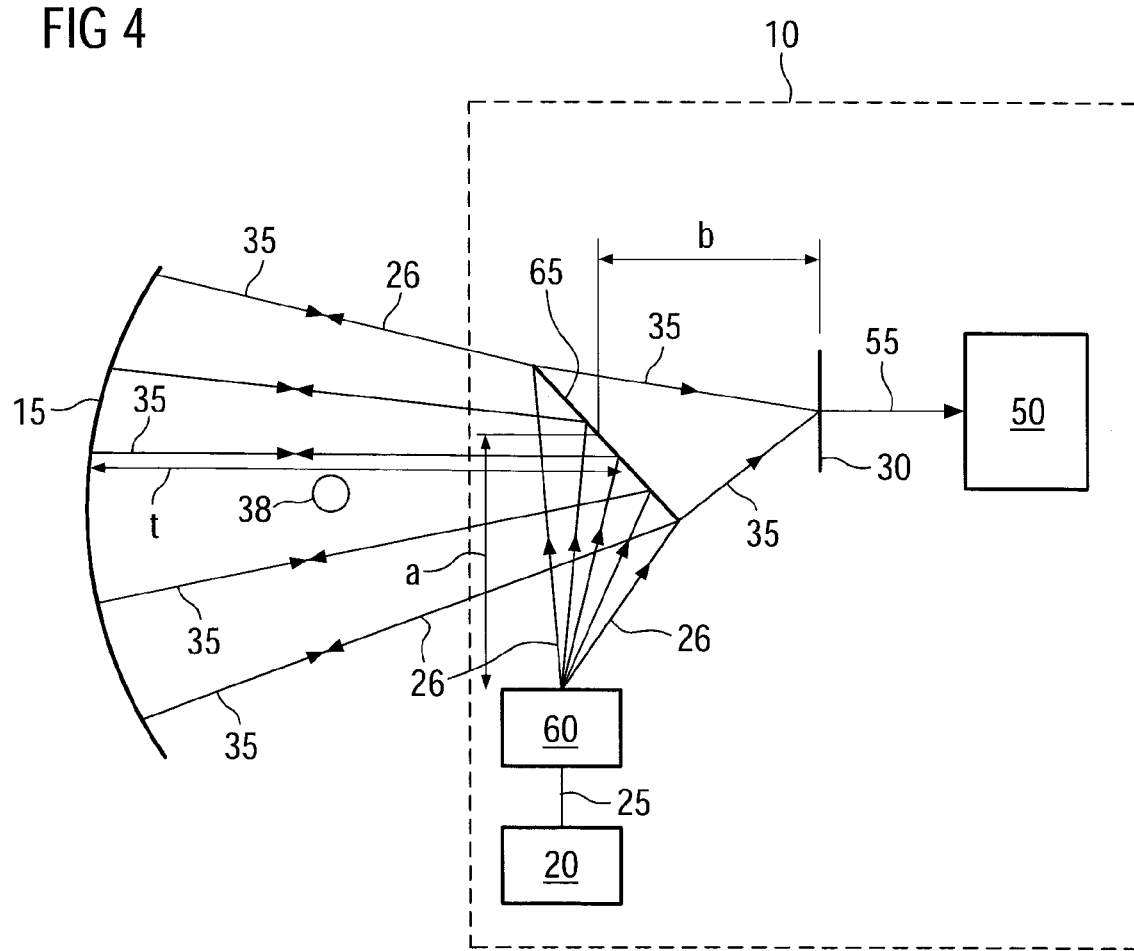
FIG. 4 depicts a schematic exemplary diagram illustrating monitoring of a reflection efficiency of a parabolic reflector using an apparatus according to an embodiment.

FIG. 4 is a schematic exemplary diagram illustrating monitoring of a reflection efficiency of a parabolic reflector using the apparatus 10 of FIG. 3 according to an embodiment. As illustrated in the example of FIG. 4, according to an aspect, the light beam 25 emitted by the light source 20 is received by the diffuser 60 and the diffuser 60 is adapted to diffuse the light beam 25 to provide a diffused light beam 26. Advantageously, the diffuser 60 can be adapted to diffuse the light beam 25 such as a function of a cross-section of the parabolic reflector 15. For example, the light beam 25 can be diffused such that the diffused light beam 26 is incident onto a parabolic cross-section of the parabolic reflector 15. The parabolic cross-section herein refers to the surface corresponding to the entire cross-section of the parabolic reflector 15. The beam splitter 65 is adapted to receive the diffused light beam 26 and reflect the diffused light beam 26 onto the parabolic reflector 15. The beam splitter 65 is also adapted to receive the reflected light beam 35 reflected by the parabolic reflector 15 and transmit the reflected light beam 35 to the detector 30. The beam splitter 65 is adapted to reflect the diffused light beam 26 onto the parabolic reflector 15 such that the diffused light beam 26 is incident onto at least a portion of the surface of the parabolic reflector 15 at an angle normal to the surface of the parabolic reflector 15. The detector 30 is configured to detect the reflected light beam 35 transmitted by the beam splitter 65. The processing unit 50 is operably coupled to the detector 30 to receive a signal 55 responsive to the detected light beam and configured to determine the intensity of the detected light beam. The detected intensity is compared with a reference intensity to estimate the reflection efficiency.

Referring still to FIG. 4, as mentioned previously, the direction of the surface normal varies for each point on the surface of the parabolic reflector 15 as the parabolic reflector 15 has a curved surface. Thus, the reflected light beam 35 is not retro-reflected for each point of the parabolic cross-section of the parabolic reflector 15. The term retro-reflected herein refers to the reflection of the reflected light beam to the point from where the light beam 25 is emitted. To overcome this, the light source 20 and the detector 30 are positioned such that the light source 20 and the detector 30 are positioned at a distance equal to the distance of the center of curvature from the surface of the parabolic reflector 15. Thus the light source 20 can be positioned at a first location and the detector 30 can be positioned at a second location, wherein the first location and the second location are at a distance equal to the distance of the center of curvature from the surface of the parabolic reflector 15. The use of the beam splitter 65 to reflect the diffused light beam 26 onto the parabolic reflector 15 and transmit the reflected light beam 35 to the detector achieves in detecting the reflected light beam 35 as if it is retro-reflected.

Referring still to FIG. 4, the distance of center of curvature from the surface of the parabolic reflector 15 is twice the distance f between the parabolic reflector 15 and the focal point of the parabolic reflector 15. In the shown example of FIG. 4, the first location being at a first distance equal to the center of curvature from the parabolic reflector 15 is achieved as the summation of the distance t between the surface of the parabolic reflector 15 to the splitter 65 and the distance a between the splitter 65 and the light source 20 is equal to the distance to the center of curvature from the surface of the parabolic reflector 15. Similarly, the second location being at a second distance equal to the center of curvature form the parabolic reflector 15 is achieved the summation of the distance t between the surface of the parabolic reflector 15 to the splitter 65 and the distance b between the splitter 65 and the light source 20 is equal to the distance to the center of curvature from the surface of the parabolic reflector 15. This arrangement enables in detecting the reflected light beam 35 reflected from the parabolic cross-section of the parabolic reflector 15 as if the reflected light beam 35 is retro-reflected.

Referring still to FIG. 4, advantageously, the diffuser 60 can be adapted to diffuse the light beam 25 such that the diffused light beam 26 is incident on substantially the entire parabolic cross-section of the parabolic reflector 15. Thus, for example, the diffuser 60 can be selected such that the diffused light beam 26 is incident on substantially the entire parabolic cross-section of the parabolic reflector 15. Reflection of the light beam from entire parabolic cross-section rather than a specific spot provides increased accuracy of monitoring the accumulation of dust on the surface of the parabolic reflector 15 and also overcomes any accuracy limitations of the positioning of the apparatus 10 for monitoring the reflection efficiency.

Referring still to FIG. 4, the apparatus 10 is designed such that every reading from the detector 30 gives information of a single parabolic cross-section of the parabolic reflector 15. The apparatus 10 is required to be moved longitudinally along the length of the parabolic reflector 15 to monitor the entire length L of FIG. 9 of the parabolic reflector 15. However, since we are mostly dealing with natural dust on the parabolic reflector 15, in certain aspects it can be assumed that the dust cover is uniform. Thus, in certain implementations, the monitoring of the reflection efficiency can be sampled only from a few well-spaced stations along the length L of FIG. 9 of the parabolic mirror 15.

Figure 5:
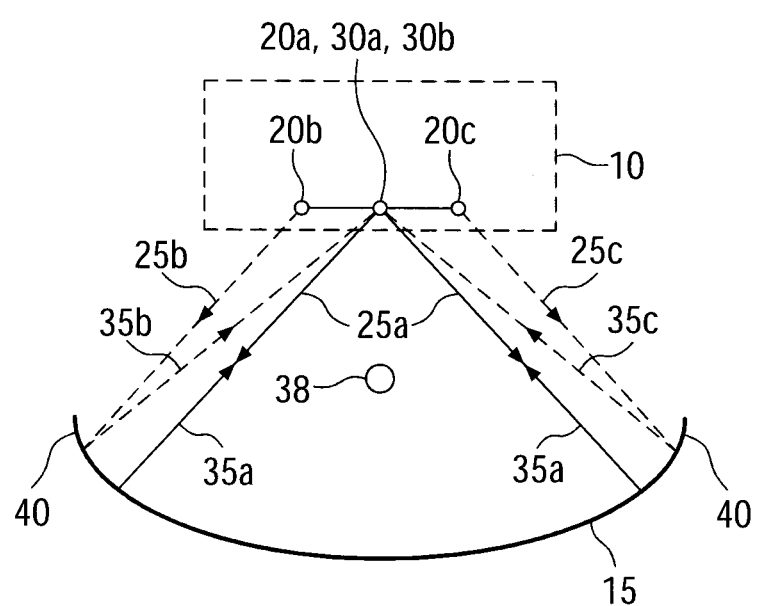
FIG. 5 depicts a schematic cross-section view of an apparatus for monitoring a reflection efficiency and alignment of the parabolic reflector to a focal point.

FIG. 5 illustrates a schematic cross-section view of an apparatus 10 for monitoring a reflection efficiency and alignment of the parabolic reflector 15 to the focal point. In the shown example of FIG. 5, the combination of the light source 20a and the detector 30a is implemented for monitoring the reflection efficiency of the parabolic reflector 15. The combination of the light sources 20b, 20c and the detector 30b is implemented for monitoring the alignment of the parabolic reflector to the focal point. In the shown example of FIG. 5, the light beam 25a emitted by the light source 20a is incident substantially onto the entire parabolic cross-section of the surface of the parabolic reflector 15. This is achieved by adapting the apparatus 10 in accordance with the embodiments described in FIG. 3 and FIG. 4. The reflected light beam 35a responsive to the incident light beam 25a is retro-reflected to the point from where the light beam 25a is emitted.

Referring still to FIG. 5, the light beams 25b and 25c emitted by the light sources 20b and 20c are incident proximal to the edges 40 of the parabolic reflector 15 as the light sources 20b and 20c are implemented for monitoring alignment of the parabolic reflector 15 to the focal length. The reflected light beams 35b and 35c responsive to the respective incident light beams 20b and 20c are detected by the detector 20b.

Figure 9:
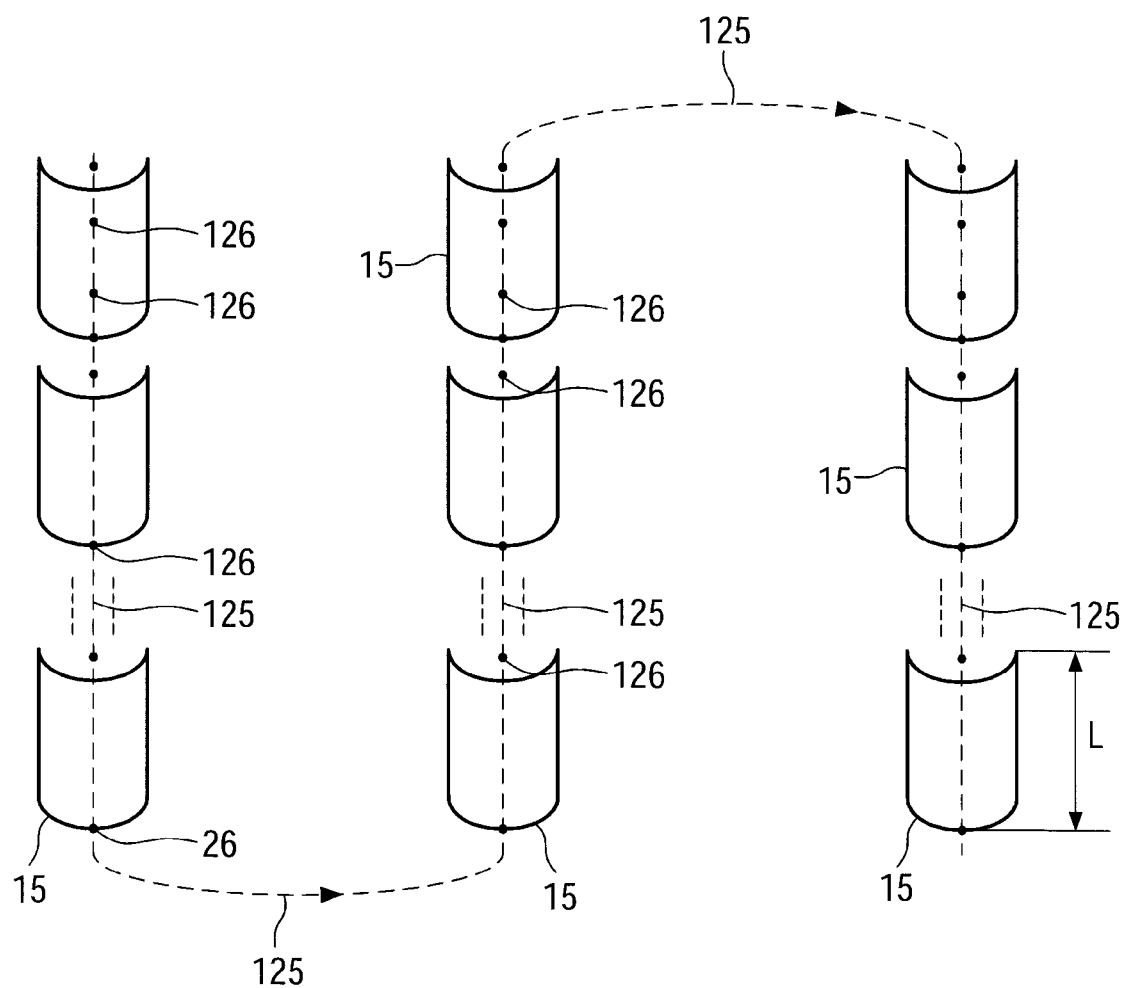
FIG. 9 depicts an exemplary schematic diagram of a solar thermal field comprising a plurality of parabolic reflectors.

Referring now to FIG. 1 to FIG. 4, for monitoring a respective parameter of the parabolic reflector 15, the apparatus 10 is required to be positioned at an appropriate location relative to the parabolic reflector 15. As mentioned previously, the apparatus 10 will advantageously be positioned beyond the focus at a height from the surface of the parabolic reflector 15 for monitoring one or more parameters. However, in case the apparatus 10 as described in FIGS. 3 to 4 is implemented for monitoring the reflection efficiency of the parabolic reflector 15, the apparatus 10 can be positioned at the center of curvature of the parabolic reflector 15. Thus, if the apparatus 10 as described in FIG. 1 or FIG. 2 is used for monitoring one or more parameters, the apparatus 10 can be positioned beyond the focus of the parabolic reflector. However, in aspects where the apparatus of FIG. 1 or 2 and FIGS. 3 to 4 is used in combination to monitor the reflection efficiency and the alignment, the apparatus 10 can be positioned at the center of curvature of the parabolic reflector 15. The entire length of the parabolic reflector is to be scanned to monitor the parabolic reflector 15. Thus, the apparatus 10 can be moved from one side of the parabolic reflector 15 to the other side so that the parabolic reflector 15 can be scanned along its entire length L (shown in FIG. 9). In the case of a solar thermal field (as shown in FIG. 9) comprising a plurality of parabolic reflectors 15, each of the parabolic reflectors 15 will be scanned along the length. To achieve this, the apparatus for 10 monitoring a parameter of the parabolic reflector 15 can be carried aerially by a system which comprises the required positioning mechanisms to position the apparatus at the desired location. For example, the system can be an unmanned aerial vehicle (UAV), tethered cable, robotic arm and the like.

Figure 6:
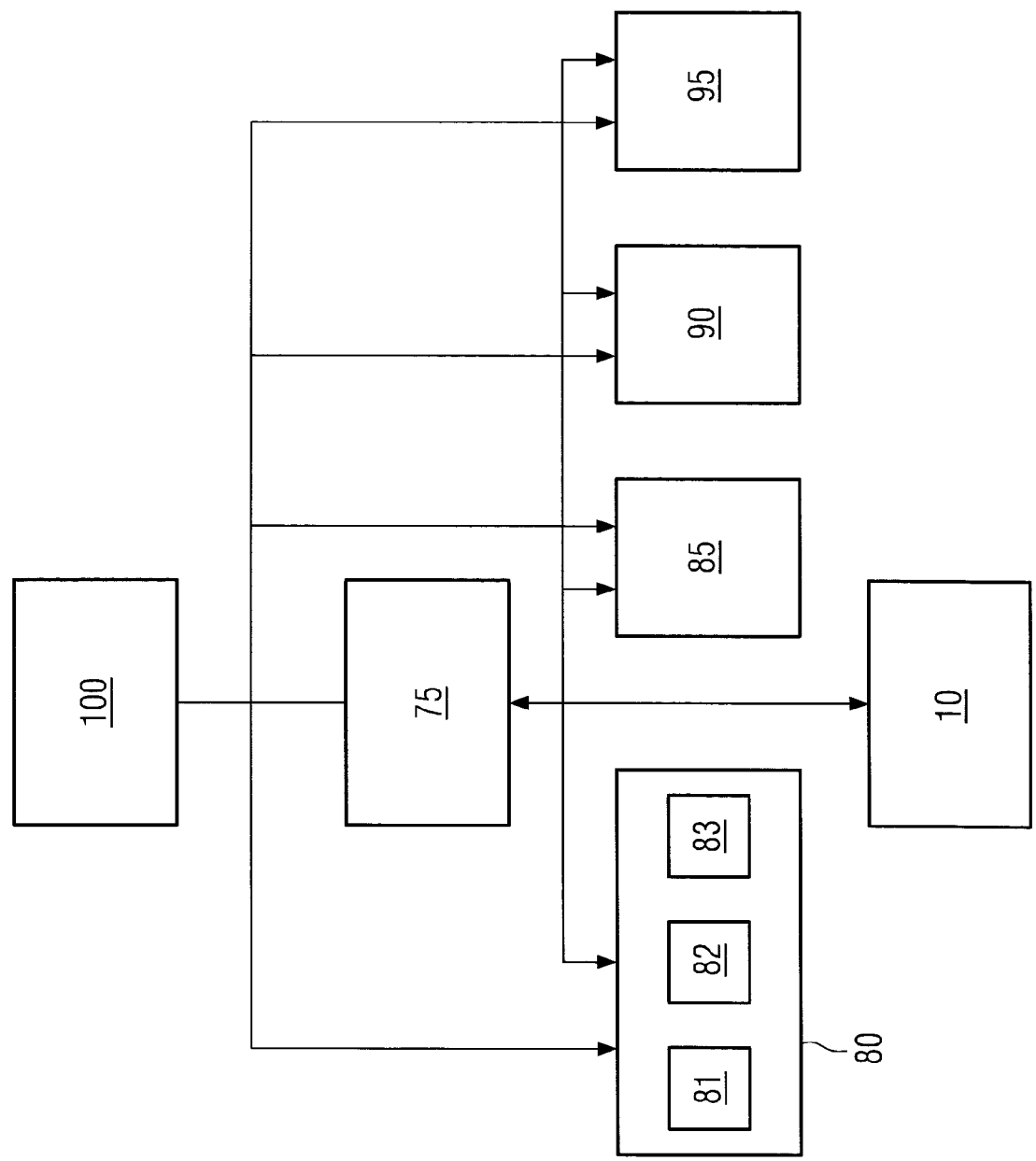
FIG. 6 depicts a schematic block diagram of a system for positioning an apparatus for aerially monitoring parabolic reflectors of a solar thermal plant according to an embodiment herein.

FIG. 6 illustrates a schematic block diagram of a system for positioning the apparatus 10 of FIG. 1 through FIG. 5 for aerially monitoring the parabolic reflectors of a solar thermal plant according to an embodiment herein. According to an aspect herein, for monitoring the parabolic reflector 15 aerially, the apparatus 10 is guided nearby the location of the parabolic reflector 15 and thereafter the apparatus 10 is positioned appropriately for monitoring the parabolic reflector 15. For example, this can be achieved by positioning the apparatus 10 at a first field location (shown as 105 in FIG. 7), and thereafter, positioning the apparatus 10 at a second field location (shown as 110 in FIG. 7) for monitoring the parabolic reflector 15. The first field location (shown as 105 in FIG. 7) will be a location nearby the parabolic reflector 15 and the second field location (shown as 110 in FIG. 7) will be determined from the first field location using information of the solar collector obtained from the first field location (shown as 105 in FIG. 7). According an aspect herein, the second field location is determined using the information of absorber tube 38. This achieves in accurate positioning of the apparatus for monitoring the parabolic reflector 15 as once the apparatus 10 is guided nearby the parabolic reflector 15, i.e., to the first field location (shown as 105 in FIG. 7), the apparatus 10 can be positioned at the second field location (shown as 110 in FIG. 7) from there for monitoring the parabolic reflector 15. The absorber tube 38 is used a marker for determining the second field location (shown as 110 in FIG. 7). The absorber tube 38 is used as the marker for positioning the apparatus 10 as the absorber tube 38 has a fixed location. This eliminates the requirement of positioning additional markers for determining the second field location (shown as 110 in FIG. 7).

Referring still to FIG. 6, the system 10 comprises the apparatus 10 as the apparatus 10 can be mounted onto the system 10 for positioning purposes. The system 70 comprises a processing module 75 operably coupled to a position estimation module 80, locomotion module 85, telemetry module 90 and a local position estimation module 95. The position estimation module 80 is configured to estimate the position and orientation of the apparatus 10 and provide information of the position and orientation of the apparatus 10 to the processing module 75. The feedback of the position and orientation of the apparatus 10 provided by the position estimation module 80 will be used for positioning the apparatus 10 at the first field location (shown as 105 in FIG. 7) relative to the parabolic reflector 15 to be monitored and also for controlling the orientation of the apparatus 10. The term "orientation" used herein is defined as angles of rotation in three dimensions of the apparatus 10 about its center of mass. The locomotion module 85 is adapted to provide movement to the apparatus 10.

Referring still to FIG. 6, according to an aspect, the locomotion module 85 can be mechanically coupled to the apparatus 10 for providing movement to the apparatus 10. Thus, according to an aspect, in case the locomotion module 85 is mechanically coupled to the apparatus 10, the position estimation module 80, the local position estimation module 95 and the apparatus 10 can be formed as one unit and the locomotion module 85 can be mechanically coupled to the unit. For example, in case a robotic arm is deployed for positioning the apparatus 10 for monitoring the parabolic reflector 15, the unit comprising the apparatus 10, the position estimation module 80 and the local position estimation module 95 will be mechanically coupled to the locomotion module 85 for providing movement to the unit. According to another aspect, the locomotion module 85 can be configured to provide movement to the system 70 and the apparatus 10 can be mounted onto the system 70. The processing module 75 based on the current position and orientation of the apparatus 10 provided by the position estimation module 80 is configured to control the locomotion module 85 such that the apparatus 10 is positioned at the first field location (shown as 105 in FIG. 7) responsive to the location of the parabolic reflector 15 with the desired orientation. Advantageously, the apparatus 10 is positioned at a height beyond the focus of the parabolic reflector 15.

Referring still to FIG. 6, for example, the information of the first field location (shown as 105 in FIG. 7) at which the apparatus 10 is to be positioned can be provided to the processing module 75 in the form of x, y, z coordinates. The x, y coordinates can be the derived from the information of the position of the parabolic reflector 15 in the x, y coordinates. The z coordinate is the height above the ground such that the first field location (shown as 105 in FIG. 7) at which the apparatus 10 is positioned is beyond the focus of the parabolic reflector 15. According to an aspect, the position estimation module 80 comprises a global positioning system (GPS) system 81, an orientation estimation system 82, and an altitude sensor 83. The GPS system 81 is implemented to provide the current position of the apparatus 10 in the x, y coordinates during the positioning of the apparatus 10. The orientation estimation system 82 is implemented to estimate the orientation of the apparatus 10 about its center of mass. Generally, in case of an aerial vehicle, the angles of rotations in three dimensions are termed as, pitch (116 of FIG. 8), roll (117 of FIG. 8) and yaw (118 of FIG. 8). Thus, pitch (116 of FIG. 8), roll (117 of FIG. 8) and yaw (118 of FIG. 8) refer to rotations about the respective axes of the aerial vehicle starting from a defined equilibrium state of the aerial vehicle. In aspects, where the apparatus 10 is positioned aerially using an UAV, the angles of rotation in three dimension of the UAV will be referred to herein as pitch (116 of FIG. 8), roll (117 of FIG. 8) and yaw (118 of FIG. 8). For example, in case the system 70 is implemented as an UAV, the orientation estimation system 82 can comprise an accelerometer, a gyroscope and a magnetometer to provide the angles of rotation in three dimensions of the UAV. The altitude sensor 83 is implemented for estimating the height of the apparatus 10 above the ground. The information of height of the apparatus 10 above the ground will be used for positioning the apparatus 10 beyond the focal point of the parabolic reflector 15.

Referring still to FIG. 6, once the apparatus 10 is positioned at the first field location (shown as 105 in FIG. 7) which is beyond the focus of the parabolic reflector 15 to be monitored, the local position estimation module 95 is adapted to acquire information of the absorber tube 38 of the parabolic reflector 15 and provide the information of the absorber tube 38 to the processing module 75. Positioning the apparatus 10 at the first field location (shown as 105 in FIG. 7) enables in acquiring the information of the absorber tube 38 as the absorber tube 38 is within the field of view of the local position estimation module 95 from the first field location (shown as 105 in FIG. 7). According to an aspect, the position of the absorber tube 38 will be used as a reference point for positioning the apparatus 10 at the second field location (shown as 110 in FIG. 7) more monitoring the parabolic reflector 15. For example, from the information of the absorber tube 38 acquired, the processing module 75 is configured to control the locomotion module 85 to control the orientation of the system 70 such that the apparatus 10 is positioned at the second field location (shown as 110 in FIG. 7) responsive to the position of the absorber tube 38. Thus, the second field location (shown as 110 in FIG. 7) is determined using the position of the absorber tube 38 as a reference point. Thus, the apparatus 10 is first positioned at the first field location (shown as 105 in FIG. 7) relative to the parabolic reflector 15 and subsequently, the apparatus 10 is positioned at the second field location (shown as 110 in FIG. 7) determined responsive to the position of the absorber tube 38. Advantageously, the second field location (shown as 110 in FIG. 7) can be such that the apparatus 10 is aligned with the absorber tube 38. Thus, the second field location (shown as 110 in FIG. 7) can be the location at which the apparatus is aligned to the absorber tube 38. However, in another implementation, the second field location (shown as 110 in FIG. 7) may not be aligned with the absorber tube 38, but can be deviated from the absorber tube 38 in a lateral direction, wherein the position of the absorber tube 38 is used as the reference point for positioning the apparatus 10 at the second field location (shown as 110 in FIG. 7).

Referring still to FIG. 6, at the second field location (shown as 110 in FIG. 7), the apparatus 10 will monitor the one or more parameters of the parabolic reflector 15. To scan the entire parabolic reflector 15, the apparatus 10 will be moved at this location along the length of the parabolic reflector 15. Thus, the apparatus 10 will monitor the parabolic reflector 15 from multiple second field locations (shown as 110 in FIG. 7) along the length of the parabolic reflector 15. The apparatus 10 can be moved along the length of the parabolic reflector 15 at the second field location (shown as 110 in FIG. 7) by varying the values of x and y coordinates and controlling the orientation of the system 70 such that the apparatus 10 is maintained at the second field location (shown as 110 in FIG. 7). The value of z coordinate will be maintained constant. The positioning of the apparatus 10 at the first field location (shown as 105 in FIG. 7) beyond the focus of the parabolic reflector 15 enables in determining the second field location (shown as 110 in FIG. 7) with ease as the information of the absorber tube 38 can be acquired easily from the first location.

According to an aspect, as explained previously, the second field location (shown as 105 in FIG. 7) to be determined can be a center of curvature of the parabolic reflector 15 and the apparatus 10 can be positioned at the center of curvature for monitoring the parabolic reflector 15. Aligning the apparatus 10 with the position of the absorber tube 38 enables in positioning the apparatus 10 at the center of curvature of the parabolic reflector 15 easily. The absorber tube 38 is usually at the focal point of the parabolic reflector 15 and the center of curvature is twice the distance of the focal point from the parabolic reflector 15. The locomotion module 85 is controlled by the processing module 75 to control the orientation of the system 70 to position the apparatus 10 at the second field location (shown as 110 in FIG. 7). The local position estimation module 95 will be described in detail in later paragraphs below.

Referring still to FIG. 6, the apparatus will be positioned at the first field location (shown as 105 in FIG. 7) using the x, y, z coordinates. The GPS system 81 of the position estimation module 80 is configured to estimate the x, y coordinates of the apparatus 10 and the altitude sensor 83 is configured to estimate the z coordinate of the apparatus 10 for positioning the apparatus 10 at the first field location (shown as 105 in FIG. 7). Thereafter, the apparatus 10 is positioned at the second field location (shown as 110 in FIG. 7) by controlling the orientation of the apparatus 10 responsive to the position of the absorber tube 38. The z coordinate of the apparatus 10 at the second field location (shown as 110 in FIG. 7) will be the same as that of the first field location (shown as 105 in FIG. 7) as the apparatus 10 can be positioned at the desired height above the surface of the parabolic reflector 15 at the first field location (shown as 105 in FIG. 7) itself.

Referring still to FIG. 6, the telemetry module 90 is configured for transmission of data between the processing module 70 and a remote station or a device. For, example, the telemetry module 90 can be used to transmit the position information of the apparatus 10 and the position of the absorber tube 38 to a remote station and can be used for providing data sent from a remote station to the processing module 75. The charge information of the battery can also be sent using the telemetry module 90 to a remote station. The telemetry module 90 can be configured to transmit data wirelessly or via wire as desired. The system 70 also comprises a power source 100 for providing power for the operation of the processing module 75 and the modules 80, 85, 90, 95 of the system 70. Advantageously, as the system 70 and the apparatus 10 will be used in combination, the processing module 75 can be configured to perform the functions of the processing unit 50. To achieve this, as illustrated in FIG. 6, the processing module 75 can be operably coupled to the detector 30. In this case, the processing module 75 will be configured for controlling the location module 85 for positioning of the apparatus 10 and for estimating one or more parameters of the parabolic reflector 15. The telemetry module 90 coupled to the processing module can be configured for transmitting the values of the parameters estimated by the processing module 75 to the remote station for further analysis of the parameters.

Referring still to FIG. 6, the system 70 can be deployed as an UAV, a robotic arm and the like for positioning of the apparatus 10 for monitoring the parabolic reflector 15. Having the system 70 deployed as an UAV provides the advantage of easy positioning of the apparatus 10 with less manual intervention. For example, if the system 70 is deployed as an UAV, the apparatus 10 can be mounted onto the UAV and the position of the UAV can be controlled to position the apparatus 10 at the first field location (shown as 105 in FIG. 7) and subsequently at the second field location (shown as 110 in FIG. 7) for monitoring the parabolic reflector 15. In aspects, where the system 70 is implemented as a robotic arm for positioning the apparatus 10, the locomotion module 85 can be mechanically coupled to a unit comprising the apparatus 10, the position estimation module 80 and the local position estimation module 95.

Referring still to FIG. 6, according to another aspect, the locomotion module 85 can be remotely controlled to position the apparatus 10 at the first field location (shown as 105 in FIG. 7) and thereafter, subsequently at the second field location (shown as 110 in FIG. 7). The feedback on information of the position of the apparatus 10 can be provided to the remote station or a device and instructions for controlling the position of the apparatus 10 can be provided to the processing unit 75 from the remote station via the telemetry module 90. For example, an operator can view the current position of the apparatus 10 provided by the position estimation module 80 and can provide instructions to the processing unit 75 for controlling the locomotion module 85 for positioning the apparatus 10 at the first field location (shown as 105 in FIG. 7) relative to the parabolic reflector 15. Once the apparatus 10 is positioned at the first field location (shown as 105 in FIG. 7), the second field location (shown as 110 in FIG. 7) at which the apparatus 10 is to be positioned for monitoring the parabolic reflector 15 is determined responsive to the position of the absorber tube 38 and the operator can provide instructions to the processing module 75 for controlling the locomotion module 85 for controlling the orientation of the apparatus 10 for positioning the apparatus 10 at the second field location (shown as 110 in FIG. 7).

Referring still to FIG. 6, according to an embodiment, the local position estimation module 95 comprises an imaging device configured to acquire an image of the absorber tube 38 and provide the acquired image to the processing module 75. The processing module 75 is configured to control the locomotion module 85 for controlling the orientation of the system 70 responsive to the position of the absorber tube 38 in the acquired image for positioning the apparatus 10 at the second field location (shown as 110 in FIG. 7) For example according to an aspect, the imaging device of the local position estimation module 95 can be such that the field of view of the device is configurable. Thus initially, the absorber tube 38 can be imaged using a wide field of view, and thereafter, the location module 85 can be controlled responsive to the image of the absorber tube 38 obtained using wide field of view of the imaging device to provide movement such that the absorber tube 38 is aligned within the narrow field of view of the imaging device of the local position estimation module 95. Thereafter, the locomotion module 85 can be controlled to provide movement such that the absorber tube 38 is aligned to a reference coordinate of the narrow field of view of the imaging device resulting in positioning the apparatus 10 at the second field location (shown as 110 in FIG. 7). The reference coordinate can be determined corresponding to the second field location at which the apparatus 10 is to be positioned. For example, the reference coordinate can correspond to the center of the narrow field of view to that that absorber tube is aligned to the center of the narrow field of view. Aligning the absorber tube 38 to the center of the narrow field of view of the imaging device enables in positioning the apparatus 10 at the second field location (shown as 110 in FIG. 7) such that the apparatus 10 is aligned with the absorber tube 38. However, in certain aspects, the apparatus 10 may not be required to be aligned with the absorber tube 38, but may be required to be at a deviation from the absorber tube 38 in the lateral direction. In such cases, the absorber tube 38 may not be aligned to be at the center of the narrow field of view of the imaging device but at a deviation in the lateral direction from the center of the narrow field of view of the imaging device.

Referring still to FIG. 6, in another implementation a wide field of view imaging device and a narrow field of view imaging device can be implemented to perform the same function. Advantageously, an infrared imaging device can be used as the imaging device for obtaining the image of the absorber tube 38 using narrow field of view. Infrared imaging provides the advantage of imaging even during night when it is dark. According to another aspect, the local position estimation module 95 can comprise a wide field of view imaging device and a transmitter and receiver to be implemented for detecting the absorber tube in the narrow field of view. The transmitter and receiver can be implemented to detect the absorber tube using the principles, including, but not limited to time of flight, radar, ultrasound (intensity based or time of flight), sonar and the like.

Figure 7:
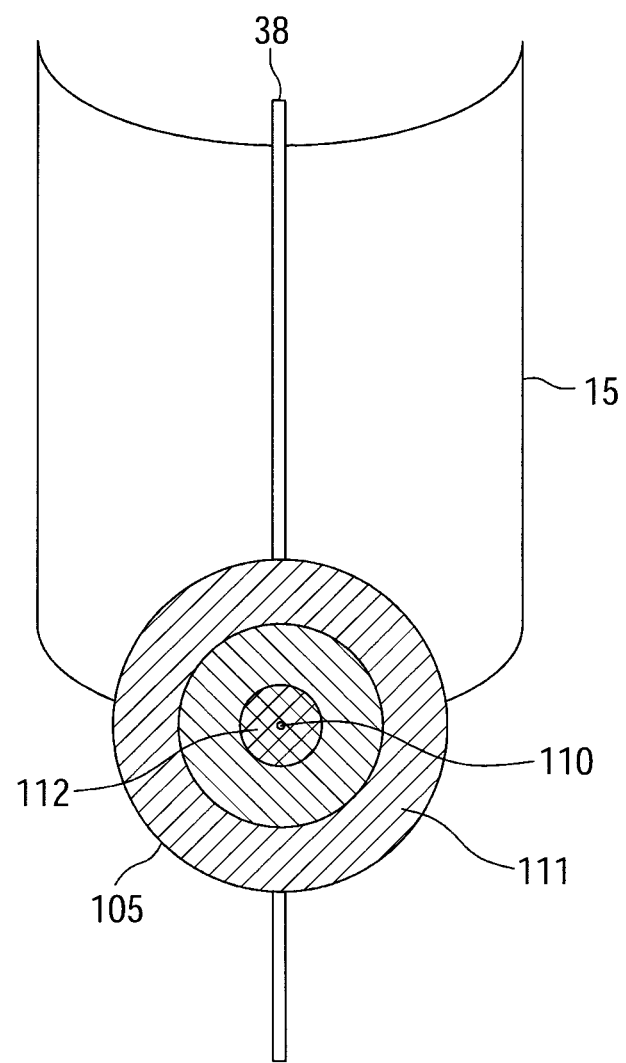
FIG. 7 depicts a schematic diagram illustrating the positioning of an apparatus at the center of curvature of a parabolic reflector according to an embodiment herein.

FIG. 7 is a schematic diagram illustrating the positioning of the apparatus 10 of FIGS. 1 to 4 at the center of curvature of the parabolic reflector according to an embodiment herein. In the shown example of FIG. 7, the system 70 of FIG. 6 is deployed as an UAV for positioning of the apparatus 10 for monitoring one or more parameters of the parabolic reflector 15. The system 70 is positioned at the first field location, designated as 105, relative to the parabolic reflector 15. The system 70 is positioned at the first field location 105 using the feedback of the current position of the system 70 provided by the position estimation module 80 of FIG. 6. The x, y coordinates corresponding to current position of the system 70 are obtained using the GPS system 81 of FIG. 6 of the position estimation module 80. As the accuracy of GPS systems is generally about 4 to 5 meters, the accuracy of positioning the system 70 at the first field location 105 may be of 4 to 5 meters. Due to this, the first field location 105 is illustrated as the hatched portion 105. Thereafter, the system 70 is required to be positioned at the second field location, designated as 110, for the apparatus 10 to monitor the parabolic reflector 15. The inaccuracy of the GPS system 81 is compensated in the embodiments herein as the local position estimation module 95 of FIG. 6 is used for positioning the system 70 at the second field location 110, which is the desired location for monitoring the parabolic reflector 15. The second field location 110 in the example of FIG. 7 is the center of curvature of the parabolic reflector 15. As illustrated in the example of FIG. 7, for positioning the system 70 at the second field location 110, the absorber tube 38 is imaged using the wide field of view, designated as the hatched portion 111, from the first field location 105. Thereafter, the system 70 is aligned such that the absorber tube 38 is within the narrow field of view, designated as the hatched portion 112, of the imaging device of the local position estimation module 95. Thereafter, the system 70 is controlled such that the absorber tube 38 is aligned to the center of the narrow field of view 112 of the imaging device of the local position estimation module 95. Aligning the absorber tube 38 within the narrow field of view 112 and to the center of the narrow field of view 112 of the imaging device includes controlling the locomotion module 85 to control the orientation of the system 70 such that the absorber tube 38 is aligned to the center of the narrow field of view 112 of the imaging device. Thus, the aligning the absorber tube 38 to the center of the narrow field of view 112 of the imaging device of the local position estimation module 95 achieves in positioning the system 70 such that the apparatus 10 is positioned at the center of curvature of the parabolic reflector 15, i.e., the second location 110.

Referring now to FIG. 1 through FIG. 7, thus, in the embodiments described herein, the information of the absorber tube 38 is used for positioning the apparatus 10 for monitoring the parabolic reflector 15. As mentioned previously, the GPS system 81 is not so accurate and thus, cannot be used for positioning of the apparatus 10 at the desired position for monitoring the parabolic reflector 15. Thus, in the embodiments described herein, the system 70 is positioned at the first field location 105 approximately, and thereafter, can be positioned at the second field location 110 which is the desired location for monitoring the parabolic reflector 15. Thus, the GPS system 81 is used for guiding the system 70 to fly nearby the parabolic reflector 15, i.e., the first field location 105 and then the system 70 is positioned at the second field location 110 for monitoring the parabolic reflector 15.

Figure 8:
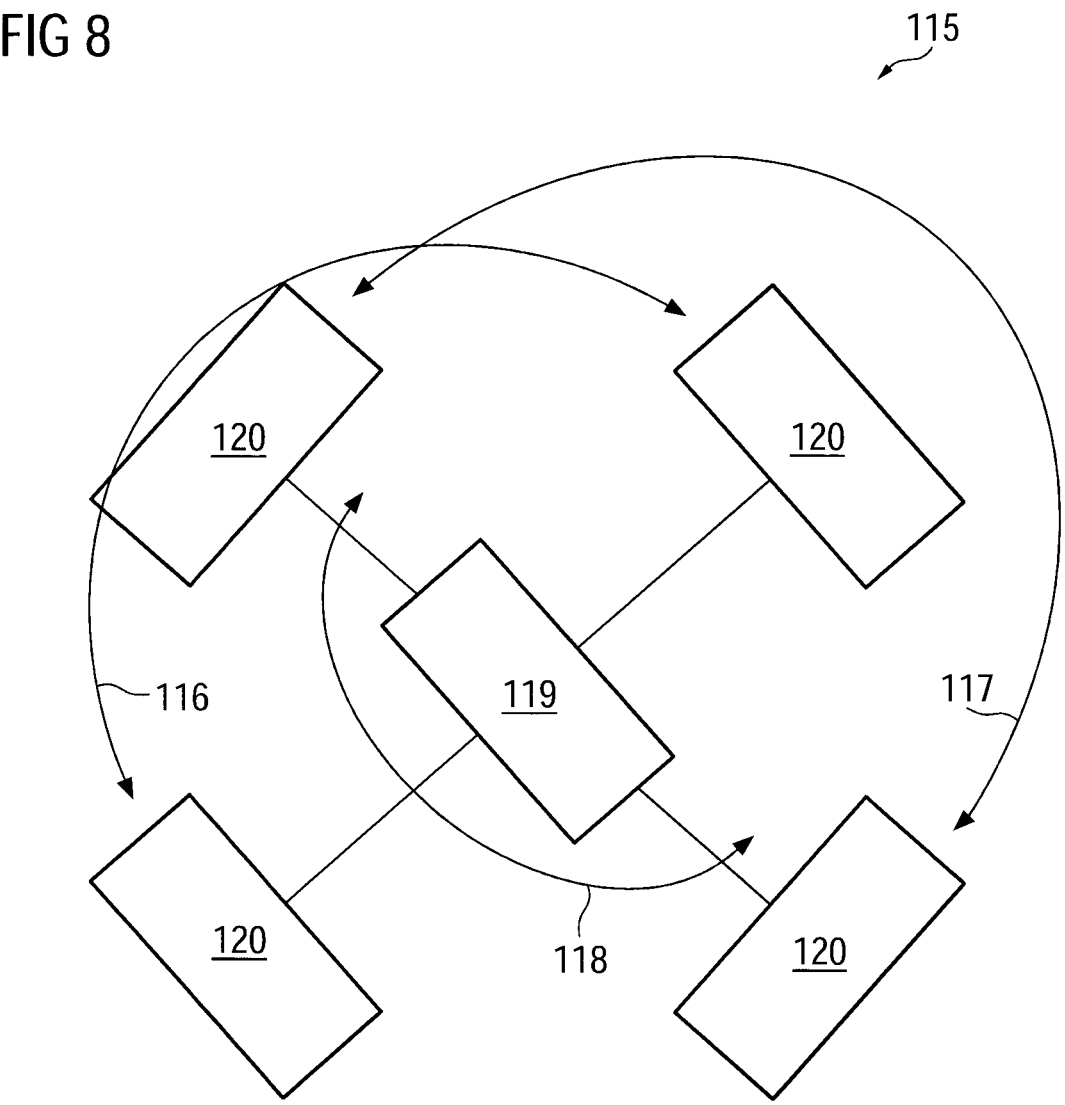
FIG. 8 depicts an exemplary diagram of an UAV deployed as a system 70 of FIG. 6 for aerially positioning an apparatus for monitoring one or more parabolic reflectors of a solar thermal field according to an embodiment herein.

The aerial positioning of the apparatus 10 for monitoring the parabolic reflector 15 will be described in detail using an UAV. FIG. 8 with reference to FIG. 1 through FIG. 7 illustrates an exemplary diagram of an UAV 115 deployed as the system 70 of FIG. 6 for aerially positioning the apparatus 10 of FIG. 1 through FIG. 5 for monitoring one or more parabolic reflectors 15 of FIG. 1 of a solar thermal field (120 of FIG. 9) according to an embodiment herein. The UAV 115 being deployed as the system 70 is an example of monitoring the parabolic reflector 15 aerially. For example, considering the requirements of the apparatus 10, the UAV 115 is required to be of about half a meter and a payload of around 500 gms. The UAV 115 flies along the length of the parabolic reflector 15, collecting and recording data on reflection efficiency and alignment of the parabolic reflector 15 to the focus on its way. The parabolic shape of the parabolic reflector 15 posses stringent requirements on the position of the apparatus 10 with respect to the parabolic reflector 15. The UAV 115 is required to fly over the parabolic reflector 15 surface at a height accurate up to a few centimeters so that the apparatus 10 can monitor the parabolic reflector 15. Similar accuracy is required in the lateral direction. This accuracy is required because of the parabolic shape of the parabolic reflector 15 as the light beam 25 incident onto the surface of the parabolic reflector is not retro reflected. Thus, to address this, the light source 20 and the detector 30 are arranged into the apparatus 10 such that the reflected light beam 35 reflected by the surface of the parabolic reflector 15 is incident onto the detector 30. The reflected light beam 35 is incident onto the detector 30 only at a distance from the surface of the parabolic reflector 15. The light source 20 and the detector 30 are arranged into the apparatus 10 taking into account this distance from the surface of the parabolic reflector 15. Thus, positioning the apparatus 10 at a height above the surface of the parabolic reflector 15 achieves in taking care of this distance. This necessitates very accurate position control by the UAV 115 so that the apparatus 10 is positioned at the second field location (110 of FIG. 7) for monitoring the parabolic reflector 15.

Referring still to FIG. 8, the orientation of the UAV 115 plays an important role for positioning of the apparatus 10 for monitoring the parabolic reflector 15. As the apparatus 10 is arranged onto the UAV 115, the orientation of the apparatus 10 will be the orientation of the UAV 115. 5. Error in pitch 116 and roll 117 angles tends to move the apparatus 10 away from the focal point of the parabolic reflector 15 as the UAV 115 is moved away from the focal point. Moreover, error in yaw 118 tends to increase the area of incidence of the reflected light beam 35 at the detector 30. This results in larger area of incidence of the reflected light beam being 35 than the area of the detector 30. With these positioning and orientation requirements, advantageously the UAV 115 is a hovering UAV. In the shown example of FIG. 8, the UAV 115 is a quadrotor UAV for positioning the apparatus 10 for monitoring one or more parabolic reflectors 115 of the solar thermal field (120 of FIG. 9). The quadrotor UAV 115 has a body 119 that is lifted and propelled by four rotors 120. The UAV 115 is controlled by varying the speeds of these four rotors 120. The locomotion module 85 of FIG. 6 of the system 70 of FIG. 6 in the present example comprises the four rotors 120 of the UAV 115. For monitoring the one or more parameters from the second field location 110 of FIG. 7, the UAV 115 can be hovered at the respective second field locations 110 of FIG. 7 along the length of the parabolic reflector 15. The UAV 115 can be hovered accurately by controlling the orientation of the UAV 115 using the feedback of the current orientation of the UAV 115 provided by the orientation estimation system 82 of FIG. 6 of the position estimation module 80 of FIG. 6. The UAV 115 being a quadrotor UAV can be hovered accurately by controlling the four rotors 120.

Still referring to FIG. 8, generally, the configuration of a UAV is under-actuated and inherently unstable. Thus, the UAV 115 has to be controlled to stabilize the flight. The flight of the UAV 115 is stabilized by controlling the orientation of the UAV 115. The orientation estimation system 82 of the position estimation module 80 estimates the angles of rotation of the UAV 115 in respective axes in three dimensions and provides the estimated angles to the processing module 75. Responsive to the estimated angles of rotation, the processing module 75 is configured to estimate the orientation of the UAV 115. Responsive to orientation estimated, the processing module 75 is configured to control the locomotion module 85 for controlling the orientation of the UAV. Thus, the orientation estimation system 82, the processing module 75 and the locomotion module 85 operate in a loop and the orientation of the UAV 115 is controllable in a continuous manner. This loop will be hereinafter referred to as the inner control loop. This achieves in controlling the orientation of the UAV 115 during its flight continuously. Thus, an algorithm for controlling the orientation can be stored at the processing module 75 or at a memory operably coupled to the processing module 75. In another aspect, the orientation can also be controlled by instructions from an operator remotely. The operator can be provided with the estimated orientation via the telemetry module 90 of FIG. 6 and the instructions from the operator can be provided to the processing module 75 for controlling the orientation of the UAV 115. With the availability of extremely small MEMS accelerometers and gyroscopes of the shelf, flight stabilization is possible with a few grams of weight and a modest computational requirement.

Referring still to FIG. 8, additionally, on top of the inner control loop, an outer control loop is programmed for navigating the UAV 115. The outer control loop would be controlling the UAV responsive to the altitude, position and path of flight. Thus, the outer control loop would require feedback of the position of the UAV 115. The GPS system 81 of FIG. 6 would provide the x, y coordinates of the current position of the UAV 115. GPS receivers are widely used for such applications and fit within the weight and power budget of a UAV. However, as discussed previously, the GPS system 81 will only provide position accuracies down to 4-5 meters. Thus, the GPS system 81 is augmented with the local position estimation module 95. The UAV 115 will be positioned at the first field location 105 of FIG. 7 using the feedback provided by the GPS system 81, and, thereafter, the UAV will be positioned at the second field location 110 of FIG. 7 using the feedback provided by the local position estimation module 95.

FIG. 9 illustrates an exemplary schematic diagram of a solar thermal field 122 comprising a plurality of parabolic reflectors 15. For monitoring the plurality of parabolic reflectors 15 of the solar thermal field 122, the UAV 115 of FIG. 8 is required to fly over the plurality of parabolic reflectors 15 of the solar thermal field 122. For flying between the parabolic reflectors 15, feedback of position information provided by the GPS system 81 of FIG. 6 will be used as the source of position information. This information is used to navigate from one parabolic reflector 15 to another parabolic reflector 15. For example, once the UAV 115 flies over the length of a parabolic reflector 15, the UAV 115 of FIG. 8 is positioned at the first field location 105 of FIG. 7 relative to the next subsequent parabolic reflector 15. Thereafter, the UAV 115 is positioned at the second field location 110 of FIG. 7 using the feedback provided by the local position estimation module 95 of FIG. 6. An example of the path 125 of the UAV 115 is illustrated in FIG. 9. The path 125 of the UAV 115 can be programmed as a series of waypoints 126 such that the UAV 115 flies over the parabolic reflectors 15 of the solar thermal field 122 for monitoring the one or more parameters. The series of waypoints 126 will be the respective second field locations 110 of FIG. 7 along the length of the parabolic reflectors 15. Various tried-and-tested navigation algorithms exist which guarantee the path-tracking with an accuracy of a few centimeters. The accuracy of the tracking depends on the forward speed with lower speed leading to better accuracy. The UAV 115 is capable of hovering as the same is a quadrotor UAV. This enables in achieving low forward speeds and thus increased accuracy of path tracking.

Referring still to FIG. 9, it has been reported in literature that quadrotor UAV's have a power consumption of about 5 watts and provide a flying endurance of about 30 minutes. A good tracking accuracy can be achieved for forward speeds of around 2 m/s. Assuming the size of an average parabolic reflector 15 to be of about 100 m, each parabolic reflector 15 can be scanned in around one minute. Around 30 parabolic reflectors 15 can then be scanned with one charge of the battery. Thus, close to 20 to 30% of average solar field 122 can be scanned with a single UAV 115 on a full battery charge. Thus, 3 to 5 flights are enough to scan the full solar thermal field 122. Since the scanning need not be done at a very high frequency, these scans can be scheduled over a period of few days. In an aspect, charging stations (not shown) can be provided in the solar thermal field 122 for charging the UAV 115. Advantageously, the charging stations can be located at predetermined locations in the solar thermal field 122 and the UAV 115 can be controlled to position itself onto a charging station for charging the battery. Thereafter, the UAV 115 can continue its scanning process of the parabolic reflectors 15.

Figure 10:
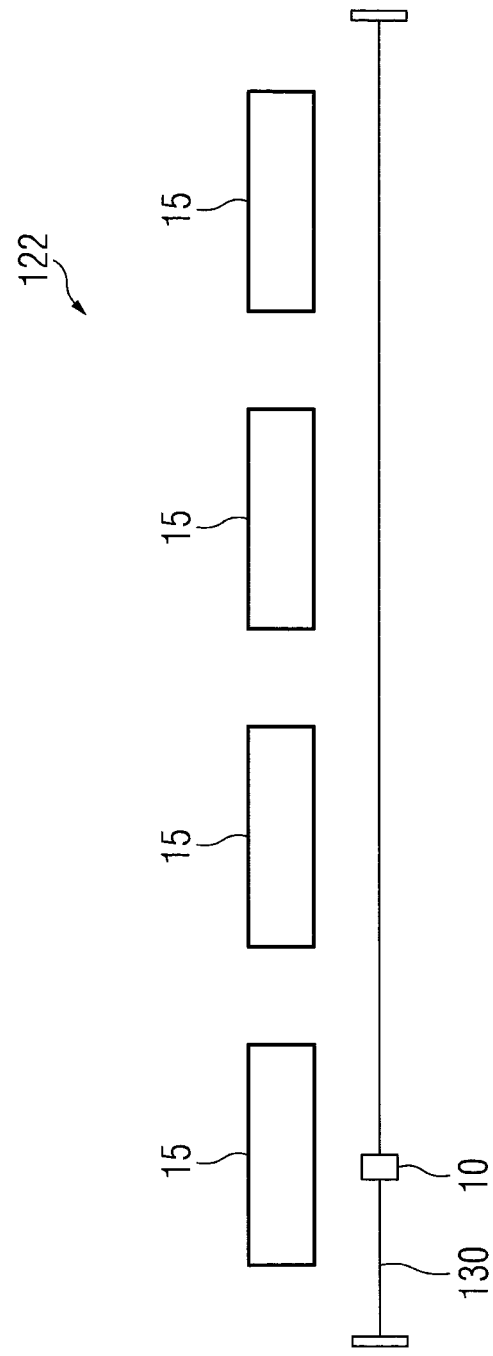
FIG. 10 depicts a top view of a schematic exemplary diagram of a tethered cable for positioning an apparatus for monitoring a solar thermal field aerially according to an embodiment herein.

According to another aspect, aerial monitoring of the parabolic reflectors 15 can also be achieved using tethered cables that can carry the apparatus 10. This greatly reduces the need for accurate control of the carrier vehicle since it is always guided. This can be either at an elevation or adjacent to the troughs at a height that is sufficient for measurements. A top view of a schematic exemplary diagram of positioning the apparatus 10 of FIG. 1 through FIG. 5 for monitoring a solar thermal field aerially using a tethered cable is illustrated in FIG. 10. In the shown example of FIG. 10, a tethered cable 130 is arranged such that the cable 130 runs along the lengths of the parabolic reflectors 15 of the solar thermal field 122. The movement of the apparatus 10 can be guided by the tethered cable 130. Advantageously, as discussed in the embodiments above, the tethered cable 130 can be arranged such that the cable 130 is beyond the focus of the parabolic reflectors 15.

Figure 11:
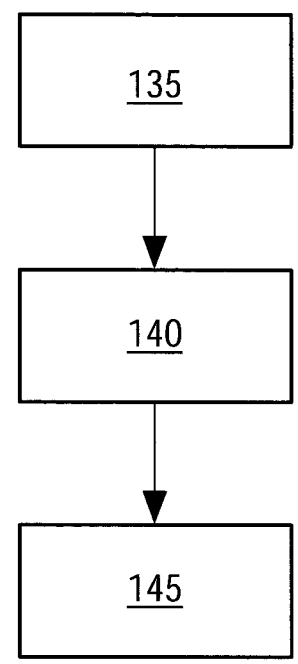
FIG. 11 depicts a method of positioning an apparatus for monitoring a parameter of one or more parabolic reflectors of a solar thermal field according to an embodiment herein.

FIG. 11 with reference to FIG. 1 through FIG. 10 is a flow diagram illustrating a method of positioning an apparatus 10 for monitoring a parameter of one or more parabolic reflectors 15 of a solar thermal field 122 according to an embodiment herein. At block 135, the apparatus 10 is positioned at a first field location 105 responsive to the position of the respective parabolic reflector 15. Next at block 140, information of an absorber tube 38 of the respective parabolic reflector 15 is acquired. Moving next to block 145, the apparatus 10 is positioned at the second field location 110 responsive to the information of the absorber tube 38, the second field location 110 being beyond the focus of the respective parabolic reflector 15.

The embodiments described in FIG. 1 through FIG. 11 can also be used for monitoring other parameters of the parabolic reflectors 15 in a similar manner by arranging additional light sources 20 and detectors 30 into the apparatus 10. The embodiments illustrated in FIG. 1 through 11 disclose monitoring of parabolic reflectors 15 of a solar power plant. In the example of FIG. 1 though FIG. 11, the parabolic reflector 15 illustrated is a parabolic trough. However, the technique described herein for positioning of the apparatus 10 for monitoring the parabolic reflector 15 can also be deployed for positioning the apparatus 10 for monitoring other types of concentrated solar power plants. However, the arrangement of the light source 20 and the detector 30 into the apparatus 10 may have to be changed for different types of concentrated solar power plants. For concentrated solar power plants deploying heliostats, the requirement of positioning the light source and the detector is less stringent.

The embodiments described herein enable positioning an apparatus for aerially monitoring one or more parabolic reflectors of a solar thermal field. Aerial monitoring provides the advantage of monitoring the solar thermal field with ease and with reduced human intervention. The positioning of the apparatus for monitoring the parabolic reflector responsive to the position of the absorber tube provides the advantage of positioning the apparatus without the requirement of additional markers. Thus, the system can be used for existing solar thermal fields without the requirement of any additional infrastructure.

EXAMPLE

Figure 12:
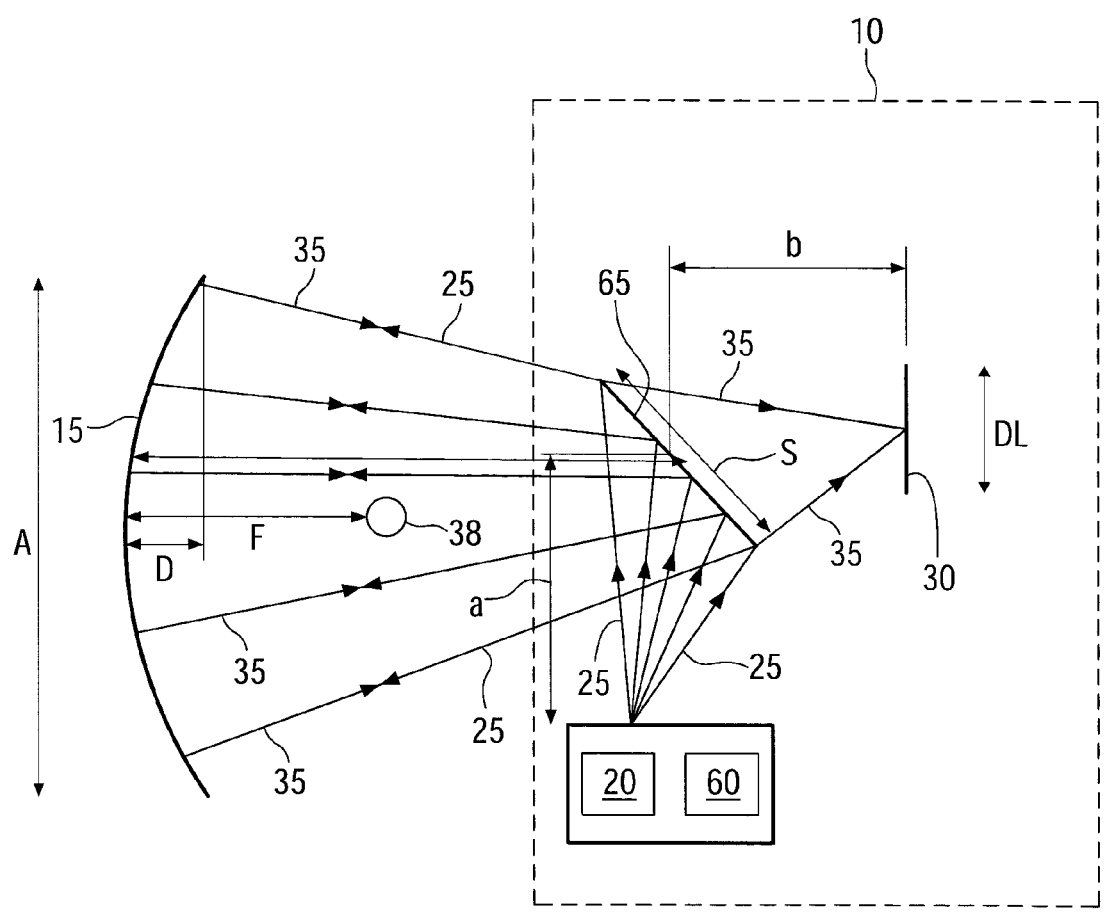
FIG. 12 depicts a schematic diagram of an apparatus.

With reference to FIG. 12, an example of calculation of dimensions and positions of the components of the apparatus 10 of FIGS. 1 to 5 is provided.

FIG. 12 with reference to FIG. 4 illustrates a schematic diagram of an apparatus 10. In the illustrated example of FIG. 12, the length A of the aperture of the parabolic reflector 15 is 5.77 m. The length L of FIG. 9 of the parabolic reflector 15 is 4 m. The focal length F is 1.71 m and the depth D of the parabolic reflector 15 is 1.21 m. The diameter d of the absorber tube 38 is 50 mm and the distance C from the parabolic reflector 15 to the center of curvature is 3.42 m. The length S of the beam slitter 65 is 50 mm and the length DL of the detector is 30 mm. The distance a between the beam splitter 65 and the light source 20 is 15 mm and the distance b between the detector 30 and the beam splitter 65 is 15 mm. Referring to the sizes and dimensions of the components of the apparatus 10 and the distances between the components, the apparatus 10 can be design in a compact manner with reduced weight. This achieves in easy positioning of the apparatus for monitoring the parameter of the parabolic reflector 15 with increased accuracy.

While this invention has been described in detail with reference to certain exemplary embodiments, it should be appreciated that the present invention is not limited to those precise embodiments. Rather, in view of the present disclosure which describes the current best mode for practicing the invention, many modifications and variations would present themselves, to those of skilled in the art without departing from the scope and spirit of this invention. The scope of the invention is, therefore, indicated by the following claims rather than by the foregoing description. All changes, modifications, and variations coming within the meaning and range of equivalency of the claims are to be considered within their scope.

The invention claimed is:

1. A method of positioning an apparatus for monitoring a parameter of one or more parabolic reflectors of a solar thermal field, the method comprising:
   positioning an apparatus for monitoring a parameter of one or more parabolic reflectors of a solar thermal field, at a first field location responsive to the position of said respective parabolic reflector, wherein the apparatus comprises a light source to direct a light beam onto at least a portion of a surface of said respective parabolic reflector, and a detector to detect the reflected light beam,
   acquiring information of an absorber tube of said respective parabolic reflector, and
   positioning the apparatus at a second field location responsive to the information of the absorber tube, the second field location being beyond the focus of said respective parabolic reflector, wherein positioning the apparatus at the second field location comprises positioning the light source and the detector, such that, the reflected light beam is incident on the detector.

2. The method according to claim 1, further comprising moving the apparatus at the second field location along a length of said respective parabolic reflector.

3. The method according to claim 1, wherein the second field location is the center of curvature of said respective parabolic reflector.

4. The method according to claim 1, wherein the step of positioning the apparatus at the second field location includes positioning the apparatus responsive to a position of the absorber tube.

5. The method according to claim 4, wherein the positioning of the apparatus responsive to the position of the absorber tube includes:
   imaging the absorber tube with a wide field of view,
   aligning the absorber tube within a narrow field of view, and
   aligning the absorber tube at a reference coordinate within the narrow field of view for positioning the apparatus.

6. The method according to claim 5, wherein the reference coordinate corresponds to a center of the narrow field of view.

7. The method according to claim 1, wherein the first field location is beyond the focus of said respective parabolic reflector.

8. The method according to claim 1, wherein the apparatus is positioned at the second field location aerially.

9. A system for positioning an apparatus for monitoring a parameter of one or more parabolic reflectors of a solar thermal field, the system comprising:
   a position estimation module configured to detect a position of an apparatus for monitoring a parameter of one or more parabolic reflectors of a solar thermal field, wherein the apparatus comprises a light source to direct a light beam onto at least a portion of a surface of said respective parabolic reflector, and a detector to detect the reflected light beam,
   a processing module operably coupled to the position estimation module to receive the detected position of the apparatus detected,
   a locomotion module operably coupled to the processing module, the processing module configured to control the locomotion module such as to position the apparatus at a first field location responsive to a position of said respective parabolic reflector, and
   a local position estimation module configured to obtain an information of an absorber tube of said respective parabolic reflector, the processing module being further configured to receive the information of the absorber tube and configured to control the locomotion module to position the apparatus at a second field location by positioning the light source and the detector, such that, the reflected light beam is incident on the detector.

10. The system according to claim 9, wherein the processing module is configured to control the locomotion module such that the apparatus is provided a motion at the second field location along a length of said respective parabolic reflector.

11. The system according to claim 9, wherein the second field location is the center of curvature of said respective parabolic reflector.

12. The system according to claim 9, wherein the processing module is configured to control the location module such that the apparatus is positioned at the second field location responsive to a position of the absorber tube.

13. The method according to claim 4, wherein the local position estimation module comprises an imaging device adapted to acquire an image of the absorber tube.

14. The system according to claim 13, wherein the imaging device comprises a configurable field of view comprising a wide field of view and a narrow field of view and the processing module is configured to control the locomotion module to align the absorber tube within the wide field of view, to align the absorber tube within the narrow field of view and to align the absorber tube to a reference coordinate within the narrow field of view.

15. The system according claim 9, wherein the system is an unmanned aerial vehicle.

\* \* \* \* \*